United States Patent
Hodgdon et al.

(10) Patent No.: US 11,723,875 B2
(45) Date of Patent: Aug. 15, 2023

(54) POLYMERIC MATERIALS AND ARTICLES MANUFACTURED THERE FROM

(71) Applicants: The Procter & Gamble Company, Cincinnati, OH (US); Virginia Tech Intellectual Properties, Inc., Blacksburg, VA (US)

(72) Inventors: Travis Kyle Hodgdon, Cincinnati, OH (US); Douglas Michael Graham, Cincinnati, OH (US); Freddy Arthur Barnabas, West Chester, OH (US); Corey James Kenneally, Mason, OH (US); Christopher Bryant Williams, Blacksburg, VA (US); Callie Elizabeth Zawaski, Blacksburg, VA (US); Timothy E Long, Blacksburg, VA (US); Allison M Pekkanen, Leesburg, VA (US); Benjamin Tyler White, Blacksburg, VA (US)

(73) Assignee: The Procter & Gamble Company, Cincinnati, OH (US)

( * ) Notice: Subject to any disclaimer, the term of this patent is extended or adjusted under 35 U.S.C. 154(b) by 1027 days.

(21) Appl. No.: 16/364,507

(22) Filed: Mar. 26, 2019

(65) Prior Publication Data

US 2019/0309238 A1 Oct. 10, 2019

Related U.S. Application Data

(60) Provisional application No. 62/655,398, filed on Apr. 10, 2018.

(51) Int. Cl.

| | | |
|---|---|---|
| *B29C 64/165* | (2017.01) | |
| *A61K 9/50* | (2006.01) | |
| *C11D 3/37* | (2006.01) | |
| *C11D 3/50* | (2006.01) | |
| *C11D 3/386* | (2006.01) | |
| *C11D 1/14* | (2006.01) | |
| *C11D 11/00* | (2006.01) | |
| *C11D 17/04* | (2006.01) | |
| *B29C 64/386* | (2017.01) | |
| *B33Y 50/00* | (2015.01) | |
| *C08G 71/04* | (2006.01) | |
| *A61K 8/87* | (2006.01) | |
| *A61K 8/02* | (2006.01) | |
| *A61K 47/34* | (2017.01) | |
| *B65D 65/46* | (2006.01) | |
| *B33Y 70/00* | (2020.01) | |
| *A61Q 19/00* | (2006.01) | |
| *A61K 9/48* | (2006.01) | |
| *B33Y 70/10* | (2020.01) | |
| *B29K 75/00* | (2006.01) | |
| *B29C 64/106* | (2017.01) | |
| *B33Y 10/00* | (2015.01) | |

(52) U.S. Cl.
CPC .......... *A61K 9/5031* (2013.01); *A61K 8/0216* (2013.01); *A61K 8/87* (2013.01); *A61K 9/4833* (2013.01); *A61K 47/34* (2013.01); *A61Q 19/00* (2013.01); *B29C 64/165* (2017.08); *B29C 64/386* (2017.08); *B33Y 50/00* (2014.12); *B33Y 70/00* (2014.12); *B33Y 70/10* (2020.01); *B65D 65/46* (2013.01); *C08G 71/04* (2013.01); *C11D 1/143* (2013.01); *C11D 3/3726* (2013.01); *C11D 3/38609* (2013.01); *C11D 3/38627* (2013.01); *C11D 3/505* (2013.01); *C11D 11/0017* (2013.01); *C11D 11/0082* (2013.01); *C11D 17/042* (2013.01); *C11D 17/044* (2013.01); *A61K 2800/56* (2013.01); *B29C 64/106* (2017.08); *B29K 2075/00* (2013.01); *B29K 2995/0062* (2013.01); *B33Y 10/00* (2014.12)

(58) Field of Classification Search
None
See application file for complete search history.

(56) References Cited

U.S. PATENT DOCUMENTS

| | | | |
|---|---|---|---|
| 4,002,598 | A | 1/1977 | Waddill |
| 4,384,951 | A | 5/1983 | Mccoy |
| 5,109,061 | A | 4/1992 | Speranza |
| 6,070,107 | A | 5/2000 | Lombardi et al. |
| 6,320,066 | B1 | 11/2001 | Audenaert |
| 6,706,852 | B2 | 3/2004 | Duan et al. |

(Continued)

FOREIGN PATENT DOCUMENTS

| | | |
|---|---|---|
| CN | 1965068 A | 5/2007 |
| CN | 101690827 A | 4/2010 |

(Continued)

OTHER PUBLICATIONS

Gregory Ellson et al. "Toough thiourethane thermoplastics for fused filament fabrication", Journal of Applied Polymer Science, vol. 135, No. 6, Feb. 10, 2018, pp. 45574-1-45574-7, XP055599159, US.

(Continued)

*Primary Examiner* — Mohammad M Ameen
(74) *Attorney, Agent, or Firm* — Angela K. Haughey; Sarah M. DeCristofaro

(57) ABSTRACT

A water-soluble polyurethane derived from: polyethylene glycol, polyethylene glycol-block-polypropylene glycol-block-polyethylene glycol polymer, polypropylene glycol-block-polyethylene glycol-block-polypropylene and mixtures thereof, 1,1'-Carbonyldiimidazole, polyamine and mixtures thereof.

6 Claims, No Drawings

Specification includes a Sequence Listing.

(56) References Cited

U.S. PATENT DOCUMENTS

| | | |
|---|---|---|
| 9,138,981 B1 | 9/2015 | Hirsch et al. |
| 2001/0025073 A1 | 9/2001 | Lombardi et al. |
| 2003/0031699 A1 | 2/2003 | Van Antwerp |
| 2003/0219591 A1 | 11/2003 | Bany |
| 2004/0116564 A1 | 6/2004 | Devlin |
| 2005/0113549 A1 | 5/2005 | Devlin |
| 2005/0276831 A1 | 12/2005 | Dihora |
| 2007/0195261 A1 | 8/2007 | Vogt |
| 2008/0045650 A1 | 2/2008 | Isobe |
| 2008/0187596 A1* | 8/2008 | Dihora .............. C11D 3/3753 424/490 |
| 2009/0171040 A1 | 7/2009 | Griswold |
| 2011/0076244 A1 | 3/2011 | Hammer |
| 2012/0224755 A1* | 9/2012 | Wu ..................... B33Y 50/00 358/1.18 |
| 2012/0226075 A1 | 9/2012 | Leutfeld |
| 2013/0281584 A1 | 10/2013 | Woutters |
| 2015/0031806 A1 | 1/2015 | Lim |
| 2016/0121597 A1 | 5/2016 | Lingier |
| 2016/0326319 A1 | 11/2016 | Breyta |
| 2017/0173872 A1 | 6/2017 | Mccall et al. |
| 2018/0009160 A1 | 1/2018 | Sawada |
| 2018/0050487 A1 | 2/2018 | Hodgdon |
| 2018/0065310 A1 | 3/2018 | Hodgdon |
| 2018/0110250 A1 | 4/2018 | Popplewell |
| 2018/0179332 A1 | 6/2018 | Priedeman, Jr. |
| 2019/0023917 A1 | 1/2019 | Drazba |
| 2019/0309163 A1 | 10/2019 | Hodgdon |
| 2020/0086551 A1 | 3/2020 | Hodgdon et al. |

FOREIGN PATENT DOCUMENTS

| | | | |
|---|---|---|---|
| CN | 103328522 A | | 9/2013 |
| CN | 103524697 A | * | 1/2014 |
| CN | 105294986 A | | 2/2016 |
| CN | 103524697 B | | 3/2016 |
| CN | 106687861 A | | 5/2017 |
| CN | 107737584 A | | 2/2018 |
| JP | 2005096199 A | | 4/2005 |
| KR | 100806677 B1 | | 2/2008 |
| WO | WO2016125860 A1 | | 8/2016 |
| WO | WO2017130685 A1 | | 8/2017 |
| WO | 2018011504 A1 | | 1/2018 |
| WO | WO2018035102 A1 | | 2/2018 |
| WO | WO2018046569 | | 3/2018 |
| WO | WO2018085066 A1 | | 5/2018 |

OTHER PUBLICATIONS

International Search Report dated Oct. 23, 2017, 6 pgs.
International Search Report, U.S. Appl. No. 16/364,497, dated May 21, 2019, 9 pgs.
International Search Report, U.S. Appl. No. 16/364,507, dated Jun. 26, 2019, 8 pgs.
Xin Wang et al., "3D Printing of polymer matrix composites: A review and prospective", Composites: Part B, vol. 110, Feb. 1, 2017, pp. 442-458, XP055598738, Amsterdam, NL.
All Office Actions; U.S. Appl. No. 15/667,654.
All Office Actions; U.S. Appl. No. 16/666,493.
All Office Actions, U.S. Appl. No. 16/364,497.
Huntsman, 'The Jeffamine Polyetheramines', Huntsman, Aug. 9, 2017, pp. 1-6, XP055463093.
Sebastian Joas et al.;"Extrusion-Based 3D Printing of Poly(ethylene glycol) Diacrylate Hydrogels Containing Positively and Negatively Charged Groups", XP055598728, dated Aug. 14, 2018, 17 Pages.
Steve R Rannard et al., "Synthesis of Water Soluble Hyperbranched Polyurethanes Using Selective Activation of AB2 Monomers", XP055598850, dated Oct. 1, 2004, 13 Pages.
Wikipedia; "Thermoplastic polyurethane", Retrieved from internet "https://en.wikipedia.org/wiki/Thermoplastic_polyirethane" Year 2019, 5 Pages.

* cited by examiner

POLYMERIC MATERIALS AND ARTICLES MANUFACTURED THERE FROM

FIELD OF THE INVENTION

The invention relates to methods and materials for manufacturing articles. The invention relates particularly to materials and methods associated with manufacturing water soluble articles from modified polyurethane materials as a sequence of voxels.

BACKGROUND OF THE INVENTION

Manufacturing articles from polymeric materials is well known in the technological arts. Manufacturing articles as a presented sequence of volume elements (voxels) derived from a digital representation of an article is also well known. That some envisioned articles may have greater utility depending upon the extent to which at least portions of the respective articles are water soluble can be envisioned. Water soluble polymers are not generally dimensionally stable enough to enable the manufacturing of objects on a voxel-by-voxel basis without a material constraining mold or support structure. In addition to dimensional stability, the ability to adjust, or tune, the rate at which an article dissolves when in use, and the ability to process the material into an article at temperatures at or below the respective boiling points of carrier solvents such as water and alcohol, is also beneficial to preserve the nature of temperature sensitive benefit agents. What is needed is a polymeric material which is both dimensionally stable enough to enable the creation of objects by fabricating a series of voxels according to a digital representation of the desired object at temperatures which preserve the utility of benefit agents, as well as soluble in an aqueous environment to yield the desired advanced utility; and a method for manufacturing articles from such a material.

SUMMARY OF THE INVENTION

In one aspect, a method for manufacturing a three-dimensional object includes steps of: a) providing a digital description of the object as a set of voxels; b) sequentially creating an actual set of voxels corresponding to the digital set of voxels; wherein at least one voxel comprises a water-soluble polyurethane derived from: polyethylene glycol, polyethylene glycol-block-polypropylene glycol-block-polyethylene glycol polymer, polypropylene glycol-block-polyethylene glycol-block-polypropylene and mixtures thereof, 1,1'-Carbonyldiimidazole, polyamine of the structure:

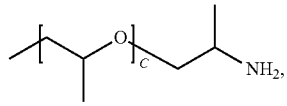

where $R_1$ is selected from the group consisting of: —OCH3, —OH, —NH2,

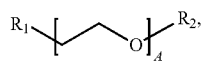

and mixtures thereof, $R_2$ is selected from the group consisting of: —(C2H4)-NH2, —CH3, —H,

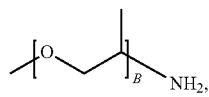

and mixtures thereof, A is between about 1 and about 300, (B+C)/A is between about 0 and about 0.6, and at least one $R_1$ or $R_2$ group contains nitrogen.

In one aspect, an article comprises a water-soluble polyurethane derived from: a water-soluble polyurethane derived from: polyethylene glycol, polyethylene glycol-block-polypropylene glycol-block-polyethylene glycol polymer, polypropylene glycol-block-polyethylene glycol-block-polypropylene and mixtures thereof, 1,1'-Carbonyldiimidazole, polyamine of the structure:

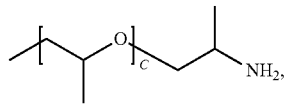

where $R_1$ is selected from the group consisting of: —OCH3, —OH, —NH2,

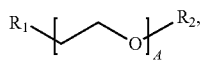

and mixtures thereof, $R_2$ is selected from the group consisting of: —(C2H4)-NH2, —CH3, —H,

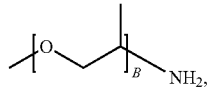

and mixtures thereof, A is between about 1 and about 300, (B+C)/A is between about 0 and about 0.6, and at least one $R_1$ or $R_2$ group contains nitrogen. In one aspect, a composition comprises a water-soluble polyurethane derived from: a water-soluble polyurethane derived from: polyethylene glycol, polyethylene glycol-block-polypropylene glycol-block-polyethylene glycol polymer, polypropylene glycol-block-polyethylene glycol-block-polypropylene and mixtures thereof, 1,1'-Carbonyldiimidazole, polyamine of the structure:

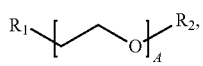

where $R_1$ is selected from the group consisting of: —OCH3, —OH, —NH2,

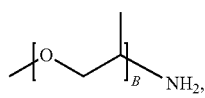

and mixtures thereof, $R_2$ is selected from the group consisting of: —(C2H4)-NH2, —CH3, —H,

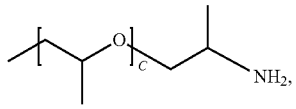

and mixtures thereof, A is between about 1 and about 300, (B+C)/A is between about 0 and about 0.6, and at least one $R_1$ or $R_2$ group contains nitrogen.

DETAILED DESCRIPTION OF THE INVENTION

In one embodiment, a method for manufacturing a three-dimensional object includes steps of: a) providing a digital description of the object as a set of voxels; b) sequentially creating an actual set of voxels corresponding to the digital set of voxels; wherein at least one voxel comprises a water-soluble polyurethane derived from: polyethylene glycol, polyethylene glycol-block-polypropylene glycol-block-polyethylene glycol polymer, polypropylene glycol-block-polyethylene glycol-block-polypropylene and mixtures thereof, 1,1'-Carbonyldiimidazole, polyamine of the structure:

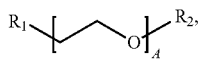

where $R_1$ is selected from the group consisting of: —OCH3, —OH, —NH2,

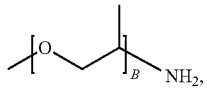

and mixtures thereof, $R_2$ is selected from the group consisting of: —(C2H4)-NH2, —CH3, —H,

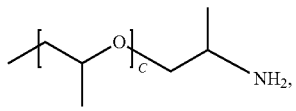

and mixtures thereof, A is between about 1 and about 300, (B+C)/A is between about 0 and about 0.6, and at least one $R_1$ or $R_2$ group contains nitrogen.

The digital description of the object as a set of voxels may be the result of a digital design process using computer aided design software to create a representation of the object. In one embodiment, the digital description may be result of scanning an object to create a digital representation of the object. The initial scanning of the object may result in a digital file which may be enhanced or otherwise altered using appropriate software. In one embodiment, a set of two dimensional images may be interpolated to yield a three-dimensional representation of the object as an array or sequence of voxels. The digital description may be provided as a .stl or other known file format.

The provided digital description may be translated to an actual object by the creation of an actual set of voxels corresponding to the set of voxels in the digital representation. This translation may be accomplished using known additive manufacturing techniques including material extrusion techniques, and those techniques referred to as 3D printing, or three dimensional printing techniques. Exemplary apparatus for the translation include fused deposition modeling (FDM) where each digital voxel is translated to an actual voxel by depositing a single liquid drop of material from a nozzle onto a build platform that freezes, cures or hardens to form the actual voxel. The nozzle and/or build-platform move to allow for at least three dimensions of orthogonal motion relative to one another. Voxels are typically deposited to form a two dimensional layer and then another layer of fluid material is deposited over the preceding layer to form the three dimensional object. The liquid droplet size and the distance between the dispensing nozzle and the proceeding layer control voxel size. Material for extrusion through the nozzle may be in a filament, pellet, powder or liquid form. A plurality of build materials may be used. It is preferred that the build-platform, nozzle and any liquid reservoir is temperature controlled. A fan may be used to aid in cooling of extruded material The final object may be post processed using any known methods including sanding, polishing and steaming to improve surface finish.

In one embodiment, each voxel of the set of voxels of the actual article is comprised of substantially the same material as all other voxels of the set. Alternatively, respective portions of the overall set of voxels may be comprised of differing materials.

At least one voxel of the set of voxels in the actual object resulting from the translation, comprises a water-soluble polyurethane derived from: polyethylene glycol (PEG), polyethylene glycol-block-polypropylene glycol-block-polyethylene glycol polymer (PEO-PPO-PEO), polypropylene glycol-block-polyethylene glycol-block-polypropylene (PPO-PEO-PPO) and mixtures thereof, 1,1'-Carbonyldiimidazole, and a polyamine of the structure:

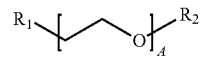

where $R_1$ is selected from the group consisting of: —NH2,

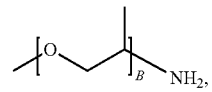

and mixtures thereof, $R_2$ is selected from the group consisting of: —(C2H4)-NH2,

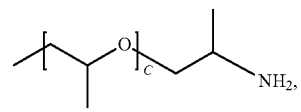

and mixtures thereof, A is between about 1 and about 300, (B+C)/A is between about 0 and about 0.6; and urea.

In one embodiment, the polyethylene glycol has an average molecular weight of about 2,000 AMU (average of 44.4 ethylene oxide repeat units) to about 35,000 AMU (average of 777 ethylene oxide repeat units). In one embodiment, the polymer comprises a PEG having an average molecular weight of about 6000 AMU (average of 135 ethylene oxide repeat units). In one embodiment, the polymer comprises a PEG having an average molecular weight of about 10,000 AMU (average of 226 ethylene oxide repeat units).

In one embodiment, the PEO-PPO-PEO and PPO-PEO-PPO polymers are Pluronics® commercially available from BASF.

In one embodiment, the polyamine is 2,2'-(Ethylenedioxy)bis(ethylamine). In one embodiment, the polyamine is O,O'-Bis(2-aminopropyl) polypropylene glycol-block-polyethylene glycol-block-polypropylene glycol polymer commercially available under the tradenames JEFFAMINE® ED600, ED900 and ED2003. In one embodiment, the polyamine comprises poly(ethylene glycol)-block-poly(propylene glycol) bis(2-amiopropyl ether) available under the tradenames JEFFAMINE® M-1000 and M-2070.

The polymer may further comprise a linker which is a monomer capable of forming two or more urea bonds when reacted with primary amines. In one embodiment, the linker is urea. In another embodiment, the linker is a molecule comprising two or more isocyanate moieties. In one embodiment, the linker is a diisocyanate. Examples of diisocyanates include methylene diphenyl diisocyanate, toluene diisocyanate, hexamethylene diisocyanate and isophorone diisocyanate. Mixtures of linkers can be used.

The voxel further comprises between about 0 and about 65 weight percent (wt. %) of a filler, wherein the filler is a solid at temperatures greater than the melting, processing and printing temperature of the overall composition. Fillers may be organic, inorganic or of mixed inorganic/organic nature. Suitable fillers are selected from the group consisting of: starches, gums, water soluble polymers, water degradable polymers, water insoluble polymers, sugars, sugar alcohols, inorganic particles, surfactants, fatty amphiphiles and mixtures thereof.

Starches may be sourced from plant materials including: corn, wheat, potato, rice, cassava and tapioca. Starches may be unmodified, modified, or partially degraded. Modified starch may include cationic starch, hydroxyethyl starch, carboxymethylated starch, and polylactic acid graft-starch and polycaprylactone graft starch. Degraded starches may include dextrin and maltodextrin preferably with a dextrose equivalent of 30 or lower.

Gums can be extracted from natural sources, modified from natural sources or fermented. Suitable natural sources from gums include trees, plants, animals and seeds. Examples of natural gums include gum acacia, gum tragacanth, gum karaya, gum ghatti, nanocrylstalline cellulose, pectin, carrageenan, agar, furcellaran, konjac gum, gelatin, guar gum, locust bean gum, tara gum, cassia gum, mesquite gum, tamarind seed gum, quince seed gum, flaxseed gum, phyllium seed gum, oat gum, and microfibrillated cellulose. Gums may also be modified to create alkali cellulose, salts of carboxymethylcellulose, methylcellulose, hydroxypropyl methylcellulose, and hydroxypropyl cellulose. Examples of fermented gums are xanthan gum, dextran and pullulan.

Suitable water-soluble polymers may be synthesized using vinyl addition reaction or ring opening synthesis. Examples of vinyl addition polymers are polyvinyl alcohol, poly(acrylic acid), poly(methacrylic acid), Poly(2-dimethylamino ethyl methacrylate) methyl chloride quaternary salt, Poly(2-dimethylamino ethylacrylate) methyl chloride quaternary salt, poly(allylamine), polyacrylamide, polymethacrylamide, poly[n-(2-hydroxypropyl) methacrylamide], Poly((3-acrylamidopropyl)trimethylammonium chloride), poly(n-(2-aminoethyl) methacrylamide hydrochloride quantized salt), poly(N-isopropylacrylamide), polyvinylpyrrolidone, poly(diallyl dimethyl ammonium chloride), poly(styrenesulfonic acid), and poly(vinyl phosphoric acid). Examples of ring opening synthesized polymers include poly(2-oxazoline), poly(2-ethyl-2-oxazoline), polyethyleneimine, poly(maleic anhydride), and polyaspartic acid. Water soluble copolymers such as poly(vinyl alcohol)-co-poly (ethylene glycol) available as Kollicoat® from BASF.

Water degradable polymers typically contain an ester bond in their backbone leading to hydrolysis in water. Examples of water degradable polymers are polylactic acid, polyglycolic acid, polybutylene succinate, polycaprolactone, polybutyrate, and poly(glycolic acid-co-lactic acid).

Examples of water insoluble polymers include nylon, polystyrene, polyurethane, polyvinyl chloride, polytetrafluoroethylene, latex and polyethylene. Latex may be natural rubber or synthetic. Commonly available synthetic latexes include nitrile rubber, polychloroprene, butyl rubber, fluorocarbon rubber, polyurethane, styrene-butadiene rubber and blends thereof. Polyethylene particles are available under the tradename VELUSTROL from HOECHST Aktiengesellschaft of Frankfurt am Main, Germany.

Examples of sugars and sugar alcohols include glucose, fructose, galactose, sucrose, maltose, lactose and trehalose. Examples of sugar alcohols include erythritol, threitol, arabitol, ribitol, xylitol, mannitol, sorbitol, galactitol, iditol, volemitol, fucitol, inositol, maltitol and lactitol.

Examples of inorganic particles include silica, fumed silica, precipitated silica, talcum powder, graphite, aluminum oxide, iron oxide, antimony trioxide, copper, bentonite clay, laponite clay, aluminium silicate clay, calcium carbonate, sodium chloride, magnesium chloride, calcium chloride, tetramethyl ammonium chloride, alumina, titanium dioxide, chalk, titanium hydroxide, gypsum powder and sodium sulfate.

Examples of organic salts include choline chloride, betaine, sorbic acid, and uric acid.

Examples of surfactants can be cationic, anionic, nonionic or zwitterionic and include sodium dodecyl sulfate, sodium dodecylbenzenesulfonate, glucose amide, cetyl and trimethylammonium bromide.

Examples of fatty amphiphiles are fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxylated amines, fatty carbamates, fatty amine oxides, fatty acids, alkoxylated fatty acids, fatty diesters, fatty sorbitan esters, fatty sugar esters, methyl glucoside esters, fatty glycol esters, mono, di- and tri-glycerides, polyglycerine fatty esters, alkyl glyceryl ethers, propylene glycol fatty acid esters, cholesterol, ceramides, fatty silicone waxes, fatty glucose amides, and phospholipids.

Mixtures of fillers may be used. These mixtures can be physical blends of two or more types of fillers or two or more fillers that are melted or dissolved together to form a single filler comprising two or more materials. Suitable methods for forming filler particles include any typical method for creating powders such as grinding, milling, spray drying, roll drying, and prilling.

Every dimension of the filler particles should be smaller than the FDM printer nozzle diameter, more preferably less than 0.5 times and more preferably less than 0.1 times the FDM printer nozzle diameter. The size of filler particles can be reduced by any common method for segregating or reducing particle size including sieving, grinding, cryogenic grinding, and milling Size and shape of the filler particles can be determined by common means such as sieving through a series of mesh screens or laser diffraction. In one embodiment, the filler particles are spherical or ellipsoidal in shape. Exemplary filler particles are spherical in shape.

The melting temperature of the filler particle must be greater than the melting, processing and printing temperatures of the final mixture. Melting temperature of the filler particles may be determined through standard methods including differential scanning calorimetry or a melt point apparatus.

The composition may further comprise a plasticizing agent to tune the viscosity of the polymer composition. Some examples of suitable plasticizing agents include water, polyethylene glycol with a weight average molecular weight of 1,000 g/mol or lower, water, ethylene glycol, propylene glycol, diethylene glycol, and glycerin. In one embodiment, the plasticizing agent is present from about 1 to about 25 percent by weight or from about 2 to about 20 percent by weight or form about 5 to about 15 percent by weight of the formulation.

In one embodiment the three-dimensional object is a consumer product. Examples of consumer products include, baby care, beauty care, fabric & home care, family care, feminine care, health care products or devices intended to be used or consumed in the form in which it is sold, and is not intended for subsequent commercial manufacture or modification. Such products include but are not limited to: conditioners, hair colorants, body wash, shampoo, facial wash, and dish detergent for and/or methods relating to treating hair (human, dog, and/or cat), including bleaching, coloring, dyeing, conditioning, shampooing, styling; personal cleansing; cosmetics; skin care including application of creams, lotions, and other topically applied products for consumer use; and shaving products, products for and/or methods relating to treating fabrics, hard surfaces and any other surfaces in the area of home care, including: air care, car care, dishwashing, hard surface cleaning and/or treatment, and other cleaning for consumer or institutional use; products and/or methods relating to oral care including toothpastes, tooth gels, tooth rinses, denture adhesives, tooth whitening; over-the-counter health care including cough and cold remedies, pain relievers, pet health and nutrition, and water purification.

The composition may further comprise a benefit agent in addition to the filler particles and the polymer. The benefit agent may comprise: perfumes, pro-perfumes, finishing aids, malodor control and removal agents, odor neutralizers, polymeric dye transfer inhibiting agents builders, heavy metal ion sequestrants, surfactants, suds stabilizing polymers, dye fixatives, dye abrasion inhibitors, soil capture polymers, flocculating polymers, colorants, pigments, aversive agents such as bittering agents, anti-redeposition agents, bleach activators, bleach catalysts, bleach boosters, bleaches, photobleaches, enzymes, coenzymes, enzyme stabilizers, crystal growth inhibitors, anti-tarnishing agents, anti-oxidants, metal ion salts, corrosion inhibitors, antiperspirant, zinc pyrithione, plant derivatives, plant extracts, plant tissue extracts, plant seed extracts, plant oils, botanicals, botanical extracts, essential oils, skin sensates, astringents, etc. (e.g., clove oil, menthol, camphor, eucalyptus oil, eugenol, menthyl lactate, witch hazel distillate), anti-acne agents (salicylic acid), anti-dandruff agents, antifoaming agents, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), skin bleaching and lightening agents, (e.g., hydroquinone, kojic acid, ascorbic acid, magnesium ascorbyl phosphate, ascorbyl glucoside, pyridoxine), skin-conditioning agents (e.g., humectants and occlusive agents), skin soothing and/or healing agents and derivatives (e.g., panthenol, and derivatives such as ethyl panthenol, aloe vera, pantothenic acid and its derivatives, allantoin, bisabolol, and dipotassium glycyrrhizinate), skin treating agents (e.g., vitamin D compounds, mono-, di-, and tri-terpenoids, beta-ionol, cedrol), sunscreen agents, insect repellants, oral care actives, personal health care actives, vitamins, anti-bacterial agents, anti-microbial agents, anti-fungal agents, their derivatives, and mixtures thereof.

In one embodiment, the benefit agent is at least partially surrounded with a wall material to create a microcapsule. In one aspect, the microcapsule wall material may comprise: melamine, polyacrylamide, silicones, silica, polystyrene, polyurea, polyurethanes, polyacrylate based materials, gelatin, styrene malic anhydride, polyamides, and mixtures thereof. In one aspect, said melamine wall material may comprise melamine crosslinked with formaldehyde, melamine-dimethoxyethanol crosslinked with formaldehyde, and mixtures thereof. In one aspect, said polystyrene wall material may comprise polyestyrene cross-linked with divinylbenzene. In one aspect, said polyurea wall material may comprise urea crosslinked with formaldehyde, urea crosslinked with gluteraldehyde, and mixtures thereof. In one aspect, said polyacrylate based materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof. In one aspect, the perfume microcapsule may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof. In one aspect, one or more types of microcapsules, for example two microcapsules types having different benefit agents may be used.

In one embodiment, the benefit agent is a perfume oil and may include materials selected from the group consisting of 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, delta-damascone, alpha-damascone, beta-damascone, beta-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and beta-dihydro ionone, linalool, ethyllinalool, tetrahydrolinalool, and dihydromyrcenol. Suitable perfume materials can be obtained from Givaudan Corp. of Mount Olive, N.J., USA, International Flavors & Fragrances Corp. of South Brunswick, N.J., USA, or Quest Corp. of Naarden, Netherlands. In one aspect, the benefit agent is a perfume microcapsule.

In one embodiment, the benefit agent is encapsulated in a shell. In one embodiment, the encapsulated benefit agent is perfume oil and the shell is a polymer.

In one embodiment the benefit agent is an enzyme. Suitable enzymes include proteases, amylases, cellulases, lipases, xyloglucanases, pectate lyases, mannanases, bleaching enzymes, cutinases, and mixtures thereof.

For the enzymes, accession numbers or IDs shown in parentheses refer to the entry numbers in the databases Genbank, EMBL and Swiss-Prot. For any mutations standard 1-letter amino acid codes are used with a * representing a deletion. Accession numbers prefixed with DSM refer to microorganisms deposited at Deutsche Sammlung von Mikroorganismen und Zellkulturen GmbH, Mascheroder Weg 1b, 38124 Brunswick (DSMZ).

Protease. The composition may comprise a protease. Suitable proteases include metalloproteases and/or serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus, Bacillus alkalophilus* (P27963, ELYA_BACAO), *Bacillus subtilis, Bacillus amyloliquefaciens* (P00782, SUBT_BACAM), *Bacillus pumilus* (P07518) and *Bacillus gibsonii* (DSM14391).

(b) trypsin-type or chymotrypsin-type proteases, such as trypsin (e.g. of porcine or bovine origin), including the *Fusarium* protease and the chymotrypsin proteases derived from *Cellumonas* (A2RQE2).

(c) metalloproteases, including those derived from *Bacillus amyloliquefaciens* (P06832, NPRE_BACAM).

Preferred proteases include those derived from *Bacillus gibsonii* or *Bacillus Lentus* such as subtilisin 309 (P29600) and/or DSM 5483 (P29599).

Suitable commercially available protease enzymes include: those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark); those sold under the tradename Maxatase®, Maxacal®, Maxapem®, Properase®, Purafect®, Purafect Prime®, Purafect Ox®, FN3®, FN4®, Excellase® and Purafect OXP® by Genencor International; those sold under the tradename Opticlean® and Optimase® by Solvay Enzymes; those available from Henkel/Kemira, namely BLAP (P29599 having the following mutations S99D+S101 R+S103A+V104I+G159S), and variants thereof including BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D) all from Henkel/Kemira; and KAP (*Bacillus alkalophilus* subtilisin with mutations A230V+S256G+S259N) from Kao.

Amylase: Suitable amylases are alpha-amylases, including those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCIB 12289, NCIB 12512, NCIB 12513, sp 707, DSM 9375, DSM 12368, DSMZ no. 12649, KSM AP1378, KSM K36 or KSM K38. Preferred amylases include:

(a) alpha-amylase derived from *Bacillus licheniformis* (P06278, AMY_BACLI), and variants thereof, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

(b) AA560 amylase (CBU30457, HD066534) and variants thereof, especially the variants with one or more substitutions in the following positions: 26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(c) variants exhibiting at least 90% identity with the wild-type enzyme from *Bacillus* SP722 (CBU30453, HD066526), especially variants with deletions in the 183 and 184 positions.

Suitable commercially available alpha-amylases are Duramyl®, Liquezyme® Termamyl®, Termamyl Ultra®, Natalase®, Supramyl®, Stainzyme®, Stainzyme Plus®, Fungamyl® and BAN® (Novozymes A/S), Bioamylase® and variants thereof (Biocon India Ltd.), Kemzym® AT 9000 (Biozym Ges. m.b.H, Austria), Rapidase®, Purastar®, Optisize HT Plus®, Enzysize®, Powerase® and Purastar Oxam®, Maxamyl® (Genencor International Inc.) and KAM® (KAO, Japan). Preferred amylases are Natalase®, Stainzyme® and Stainzyme Plus®.

Cellulase: The composition may comprise a cellulase. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum*.

Commercially available cellulases include Celluzyme®, and Carezyme® (Novozymes A/S), Clazinase®, and Puradax HA® (Genencor International Inc.), and KAC-500 (B)® (Kao Corporation).

In one aspect, the cellulase can include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403), appended hereto as Sequence 1, and mixtures thereof. Suitable endoglucanases are sold under the tradenames Celluclean® and Whitezyme® (Novozymes A/S, Bagsvaerd, Denmark).

Preferably, the composition comprises a cleaning cellulase belonging to Glycosyl Hydrolase family 45 having a molecular weight of from 17 kDa to 30 kDa, for example the endoglucanases sold under the tradename Biotouch® NCD, DCC and DCL (AB Enzymes, Darmstadt, Germany).

Highly preferred cellulases also exhibit xyloglucanase activity, such as Whitezyme®.

Lipase. The composition may comprise a lipase. Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*), or from *H. insolens*, a *Pseudomonas* lipase, e.g., from *P. alcaligenes* or *P. pseudoalcaligenes, P. cepacia, P. stutzeri, P. fluorescens, Pseudomonas* sp. strain SD 705, *P. wisconsinensis*, a *Bacillus* lipase, e.g., from *B. subtilis, B. stearothermophilus* or *B. pumilus*.

The lipase may be a "first cycle lipase", preferably a variant of the wild-type lipase from *Thermomyces lanuginosus* comprising T231R and N233R mutations. The wild-type sequence is the 269 amino acids (amino acids 23-291) of the Swissprot accession number Swiss-Prot O59952 (derived from *Thermomyces lanuginosus* (*Humicola lanuginosa*)). Preferred lipases would include those sold under the tradenames Lipex®, Lipolex® and Lipoclean® by Novozymes, Bagsvaerd, Denmark.

Preferably, the composition comprises a variant of *Thermomyces lanuginosa* (O59952) lipase having >90% identity with the wild type amino acid and comprising substitution(s) at T231 and/or N233, preferably T231R and/or N233R.

In another aspect, the composition comprises a variant of *Thermomyces lanuginosa* (O59952) lipase having >90% identity with the wild type amino acid and comprising substitution(s):

(a) S58A+V60S+I83T+A150G+L227G+T231R+N233R+I255A+P256K;
(b) S58A+V60S+I86V+A150G+L227G+T231R+N233R+I255A+P256K;
(c) S58A+V60S+I86V+T143S+A150G+L227G+T231R+N233R+I255A+P256K;
(d) S58A+V60S+I86V+T143S+A150G+G163K+S216P+L227G+T231R+N233R+I255A+P256K;
(e) E1*+S58A+V60S+I86V+T143S+A150G+L227G+T231R+N233R+I255A+P256K;
(f) S58A+V60S+I86V+K98I+E99K+T143S+A150G+L227G+T231R+N233R+I255A+P256K;
(g) E1N+S58A+V60S+I86V+K98I+E99K+T143S+A150G+L227G+T231R+N233R+I255A+P256K+L259F;
(h) S58A+V60S+I86V+K98I+E99K+D102A+T143S+A150G+L227G+T231R+N233R+I255A+P256K;
(i) N33Q+S58A+V60S+I86V+T143S+A150G+L227G+T231R+N233R+I255A+P256K;
(j) E1*+S58A+V60S+I86V+K98I+E99K+T143S+A150G+L227G+T231R+N233R+I255A+P256K;
(k) E1N+S58A+V60S+I86V+K98I+E99K+T143S+A150G+S216P+L227G+T231R+N233R+I255A+P256K;
(l) D27N+S58A+V60S+I86V+G91N+N94R+D1UN+T143S+A150G+L227G+T231R+N233R+I255A+P256K;
(m) E1N+S58A+V60S+I86V+K98I+E99K+T143S+A150G+E210A+S216P+L227G+T231R+N233R+I255A+P256K;
(n) A150G+E210V+T231R+N233R+I255A+P256K; and
(o) I202L+E210G+T231R+N233R+I255A+P256K.

Xyloglucanase: Suitable xyloglucanase enzymes have enzymatic activity towards both xyloglucan and amorphous cellulose substrates, wherein the enzyme is a glycosyl hydrolase (GH) is selected from GH families 5, 12, 44 or 74. Preferably, the glycosyl hydrolase is selected from GH family 44. Suitable glycosyl hydrolases from GH family 44 are the XYG1006 glycosyl hydrolase from *Paenibacillus polyxyma* (ATCC 832) and variants thereof.

Pectate lyase: Suitable pectate lyases are either wild-types or variants of Bacillus-derived pectate lyases (CAF05441, AAU25568) sold under the tradenames Pectawash®, Pectaway® and X-Pect® (from Novozymes A/S, Bagsvaerd, Denmark).

Mannanase: Suitable mannanases are sold under the tradenames Mannaway® (from Novozymes A/S, Bagsvaerd, Denmark), and Purabrite® (Genencor International Inc., Palo Alto, Calif.).

Bleaching enzyme: Suitable bleach enzymes include oxidoreductases, for example oxidases such as glucose, choline or carbohydrate oxidases, oxygenases, catalases, peroxidases, like halo-, chloro-, bromo-, lignin-, glucose- or manganese-peroxidases, dioxygenases or laccases (phenoloxidases, polyphenoloxidases). Suitable commercial products are sold under the Guardzyme® and Denilite® ranges from Novozymes. Advantageously, additional, preferably organic, particularly preferably aromatic compounds are incorporated with the bleaching enzyme; these compounds interact with the bleaching enzyme to enhance the activity of the oxidoreductase (enhancer) or to facilitate the electron flow (mediator) between the oxidizing enzyme and the stain typically over strongly different redox potentials.

Other suitable bleaching enzymes include perhydrolases, which catalyse the formation of peracids from an ester substrate and peroxygen source. Suitable perhydrolases include variants of the Mycobacterium smegmatis perhydrolase, variants of so-called CE-7 perhydrolases, and variants of wild-type subtilisin Carlsberg possessing perhydrolase activity.

Cutinase: Suitable cutinases are defined by E.C. Class 3.1.1.73, preferably displaying at least 90%, or 95%, or most preferably at least 98% identity with a wild-type derived from one of *Fusarium solani, Pseudomonas Mendocina* or *Humicola Insolens*.

Identity. The relativity between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The polymers of the current invention are particularly useful for including benefit agents that are temperature sensitive and may otherwise be difficult to incorporate into other water soluble polymers like polyvinyl alcohol. Benefit agents that are known to be temperature sensitive include perfume, encapsulated perfume, enzymes, bittering agent, vitamins, botanical extracts and mixtures thereof.

Examples of a temperature sensitivity include boiling point, flash point, degradation, and/or denaturing. Perfumes are particularly challenging to incorporate into polymers because may of the perfume ingredients have low boiling points and/or low flash points causing loss of perfume during processing or dangerous processing conditions due to risk of fire. Enzymes are particularly challenging to incorporate into water-soluble polymers because enzymes are prone to degrading and denaturing when exposed to temperatures above room temperature. Any degradation or denaturing of an enzyme will cause a loss in activity and efficacy of the enzyme or protein.

Compositions of the present invention may contain from about 0.5 to about 35 percent by weight of a benefit agent, alternatively from about 1 to about 30 percent by weight or from about 2 to about 25 percent by weight. Compositions of the present invention my contain from about 1 to about 45 percent by weight of a filler, alternatively from about 2 to about 35 percent by weight or from about 5 to about 25 percent by weight. In one embodiment, the composition contains a poly urea polymer, at least one benefit agent and at least one filler.

In one embodiment, the three-dimensional object comprises a container filled with one or more benefit agents. The container may be comprised at least partially from the materials of the invention to provide water solubility to at least a portion of the container to release the benefit agent.

The benefit agent may comprise a single solid element, a collection of solid powder elements, a liquid or a gas. In one embodiment, the benefit agent may comprise a solid or powder and the benefit agent may enable the printing of a portion of the container directly in contact with the benefit agent, the benefit agent providing structural support for the printing, to close the container.

In one embodiment, the benefit agent is an oral care active. Suitable oral care actives include prevention agents including, but not limited to: sodium fluoride, stannous fluoride, sodium monofluorophosphate; dentinal hypersensitivity treatments including, but not limited to: potassium nitrate, strontium chloride and stannous fluoride; gingivitis prevention and treatment agents, including, but not limited to stannous fluoride, triclosan, cetyl pyridinium chloride and chlorhexidine; dental erosion prevention agents including, but not limited to: sodium fluoride, stannous fluoride and sodium polyphosphate; periodontitis treatment agents including, but not limited to chlorhexidine, tetracycline, doxycycline, and ketoprofen; dry mouth amelioration agents including, but not limited to pilocarpine, pellitorin.

In one embodiment, the benefit agent is a personal health care active. Suitable personal health care actives include Personal Health care: Cold and flu treatments including, but not limited to, Anti histamines, such as diphenhydramine hydrochloride, Doxylamine succinate, Chlorpheniramine Maleate, fexofenadine, terfenadine, cetirizine Decongestants; such as Phenylephrine Hydrochloride, Pseudoephedrine, Oxymetazoline, Expectorants, such as Guaifenesin, Cough Suppressants; such as dextromethorphan hydrobromide, Antipyretics and Analgesics, such as Acetaminophen, Ibuprofen, Naproxen, Aspirin. Antacids including but not limited to Acid reducers such as, magnesium Hydroxide, Aluminum Hydroxide, Calcium carbonate, Sodium bicarbonate, simethicone; H2 Antagonist, such as, cimetidine, ranitidine, famotidine; Proton Pump inhibitors, such as Omeprazole, Pantoprazole. Antidiarrheals including but not limited to bismuth subsalicylate, loperamide. Probiotics including but not limited to *Bifidobacterium infantis, Lactobacillus acidophilus*. Bulk forming fibers including but not limited to Psyllium.

Suitable fluorescent brighteners include: di-styryl biphenyl compounds, e.g. Tinopal® CBS-X, di-amino stilbene di-sulfonic acid compounds, e.g. Tinopal® DMS pure Xtra and Blankophor® HRH, and Pyrazoline compounds, e.g. Blankophor® SN, and coumarin compounds, e.g. Tinopal® SWN. Preferred brighteners are: sodium 2 (4-styryl-3-sulfophenyl)-2H-napthol[1,2-d]triazole, disodium 4,4'-bis{[(4-anilino-6-(N methyl-N-2 hydroxyethyl)amino 1,3,5-triazin-2-yl)];amino}stilbene-2-2'disulfonate, disodium 4,4'-bis{[(4-anilino-6-morpholino-1,3,5-triazin-2-yl)]amino} stilbene-2-2'disulfonate, and disodium 4,4'-bis(2-sulfostyryl) biphenyl. A suitable fluorescent brightener is C.I. Fluorescent Brightener 260, which may be used in its beta or alpha crystalline forms, or a mixture of these forms.

Preferred chelants are selected from: diethylene triamine pentaacetate, diethylene triamine penta(methyl phosphonic acid), ethylene diamine-N'N'-disuccinic acid, ethylene diamine tetraacetate, ethylene diamine tetra(methylene phosphonic acid) and hydroxyethane di(methylene phosphonic acid). A preferred chelant is ethylene diamine-N'N'-disuccinic acid and/or hydroxyethane diphosphonic acid.

Suitable hueing agents include small molecule dyes, typically falling into the Colour Index (C.I.) classifications of Acid, Direct, Basic, Reactive or hydrolysed Reactive, Solvent or Disperse dyes for example that are classified as Blue, Violet, Red, Green or Black, and provide the desired shade either alone or in combination. Preferred hueing agents include Acid Violet 50, Direct Violet 9, 66 and 99, Solvent Violet 13 and any combination thereof. Suitable hueing agents include phthalocyanine and azo dye conjugates, such as described in WO2009/069077.

Polymer compositions can be created by any method of mixing or blending of the molten polymer with the fillers and benefit agents. In one example, the polymer is melted in a glass jar, benefit agents and fillers added by weight and mixed by hand to create the composition.

Voxel error relates to any change in dimensional requirements of a voxel due to expansion, shrinkage or movement of the material disposed for a particular voxel from the dimensional limits of that voxel. Voxel error magnitude for any particular may be calculated as the volume percent of the voxel which is missing at the time that the last voxel of the overall translation which is adjacent to the particular voxel, is deposited.

EXAMPLES

Polymer Synthesis Example

Polymers of the current invention P1-P4 and comparative polymer CP1 were synthesized in a similar manner. In a typical synthesis, 2,000 g/mol poly(ethylene glycol) (10 g, 0.005 mol, Mn ~2,000 g/mol) and 1,1'-carbonyldiimidazole (4.05 g, 0.025 mol) were introduced into a 100 mL round-bottomed flask equipped with a magnetic stir bar. The monomers were dissolved in chloroform (50 mL), and the solution was purged with nitrogen gas. The reaction proceeded at 25 C for 30 min. The product was washed three times with deionized water and once with brine water to remove the imidazole side product. The purified product (5.0 g, 0.0022 mol) was then charged to a 100 mL round-bottomed flask with 2,2'-(Ethylenedioxy) bis(ethylamine) (6.6 g, 0.044 mol), and dissolved in chloroform (45 mL). The reaction was allowed to proceed at 25 C for 2 h under nitrogen, and the product was washed 3 times with deionized water and once with brine water.

Polymers of the current invention P5-P8 and comparative polymer CP2 were synthesized by further reacting polymers P1-P4 and CP1 with the linker urea in the following manner. The polymer (10 g, 0.0041 mol) and the linker urea (0.25 g, 0.0041 mol) were introduced into a 100 mL round-bottomed flask equipped with a metal stir rod, gas inlet, distillation apparatus, and a mechanical overhead stirrer. The reactor was degassed and purged with nitrogen three times to remove oxygen from the system. The reaction was stirred at 80 RPM under a constant nitrogen flow at 180 C for 30 min. The temperature was ramped to 200 C for 30 min and 220 C for 30 min to keep the polymer molten. After 30 min at 220 C, vacuum was applied until 0.15 mmHg and the reaction proceeded under vacuum for 2 h at 250 C. The heating source was removed, and the reaction was allowed to cool overnight under static vacuum. The polymers were removed from the round-bottomed flask and used without further purification.

Table 1 provides data regarding exemplary polymers.

TABLE 1

| Example | Monomer Type | | | | Monomer wt. % | | | |
|---|---|---|---|---|---|---|---|---|
| | A | B | C | Linker | A | B | C | Linker |
| P1 | PEG 400 (EO = 9.1) | 1,1'-Carbonyldiimidazole | 2,2'-(Ethylenedioxy)bis(ethylamine) | none | 45.8% | 37.2% | 17.0% | 0% |
| P2 | PEG 1k (EO = 22.7) | 1,1'-Carbonyldiimidazole | 2,2'-(Ethylenedioxy)bis(ethylamine) | none | 67.9% | 22.0% | 10.1% | 0% |
| P3 | PEG 2k (EO = 45.5) | 1,1'-Carbonyldiimidazole | 2,2'-(Ethylenedioxy)bis(ethylamine) | none | 80.9% | 13.1% | 6.0% | 0% |
| P4 | PEG 4k (EO = 90.9) | 1,1'-Carbonyldiimidazole | 2,2'-(Ethylenedioxy)bis(ethylamine) | none | 89.5% | 7.2% | 3.3% | 0% |
| CP1 | PEG 1k (EO = 22.7) | 1,1'-Carbonyldiimidazole | m-Xylylenediamine | none | 68.5% | 22.1% | 9.4% | 0% |
| P5 | PEG 400 (EO = 9.1) | 1,1'-Carbonyldiimidazole | 2,2'-(Ethylenedioxy)bis(ethylamine) | Urea | 43.0% | 34.8% | 15.9% | 6.4% |
| P6 | PEG 1k (EO = 22.7) | 1,1'-Carbonyldiimidazole | 2,2'-(Ethylenedioxy)bis(ethylamine) | Urea | 65.3% | 21.1% | 9.7% | 3.9% |
| P7 | PEG 2k (EO = 45.5) | 1,1'-Carbonyldiimidazole | 2,2'-(Ethylenedioxy)bis(ethylamine) | Urea | 79.0% | 12.8% | 5.9% | 2.4% |
| P8 | PEG 4k (EO = 90.9) | 1,1'-Carbonyldiimidazole | 2,2'-(Ethylenedioxy)bis(ethylamine) | Urea | 88.3% | 7.1% | 3.3% | 1.3% |
| CP2 | PEG 1k (EO = 22.7) | 1,1'-Carbonyldiimidazole | m-Xylylenediamine | Urea | 65.7% | 21.2% | 8.9% | 4.2% |

The relatively low melting and processing temperature of polymers of the current invention allows for incorporation of benefit agents. Benefit agents can be added by mixing the benefit agents with molten polymer and cooling below the compositions melt temperature. Compositions are created by combining all ingredients by weight at room temperature in a glass jar, sealing the jar, melting the composition by placing in an oven, mixing the composition using a metal spatula and allowing mixture to cool and freeze at room temperature. Examples of compositions C1-C8 of the current invention are shown in Table 3. Compositions C1-C9 can be useful, for example, as scent and cleaning boosters in the process of laundering cloths.

TABLE 2

| Ingredient | C1 | C2 | C3 | C4 | C5 | C6 | C7 | C8 | C9 |
|---|---|---|---|---|---|---|---|---|---|
| Polymer Type | P1 | P3 | P2 | P3 | P4 | P7 | P8 | P3 | P6 |
| Polymer [wt. %] | 96 | 94 | 96 | 94 | 89 | 99 | 87 | 94 | 96.5 |
| Perfume Oil [wt. %] | 2.5 | 3 | 1 | 2 | 5 | 1 | 3 | 0.5 | 2 |
| Encapsulated Perfume Oil [wt. %][1] | 0 | 2 | 2 | 0 | 1 | 0 | 3 | 2 | 1 |
| Lipase [wt. %][2] | 0 | 0 | 0 | 1 | 1 | 0 | 0 | 0.5 | 0 |
| Amylase [wt. %][3] | 0.5 | 1 | 0 | 1 | 1 | 0 | 0 | 0 | 0.5 |
| Sodium dodecyl sulfonate [wt. %][4] | 1 | 0 | 1 | 2 | 2 | 0 | 7 | 3 | 0 |

[1]Available from Encapsys
[2]Commercially available from Novozymes
[3]Commercially available from Novozymes
[4]Avaialble from SigmaAldrich Test Methods:
Melting Temperature Determination Differential scanning calorimetry (DSC) was performed on a TA instruments DSC Q2000 to determine the melting temperature of each polymer. A heat-cool-heat cycle from −90 C to 150 C at a rate of 5 C/min was performed, and the melting temperature was calculated as the maximum of the melting endotherm from the second heat.

Melt Viscosity Determination

The melt viscosity was determined using a TA instruments Ares G2 rheometer. Rheological experiments were performed in oscillation mode with 25 mm parallel plates at a constant temperature of 20 C above the melting point of the polymer as determined by DSC. Frequency sweeps were performed between 0.1-100 rad/s at a constant strain of 1%.

Time to Dissolve

Polymers films with a thickness of 0.5 mm were placed in scintillation vials equipped with magnetic stir bars. Deionized water was added to the vials such that the concentration of the polymer in water was 1 mg/mL. The polymers were stirred at room temperature, and the time to dissolve was determined by eye as the time when the film was no longer visually apparent.

FDM Printing of Mixtures

Polymers and mixtures are stored in sealed glass jars. Prior to printing, the material was melted into a high temperature syringe in a vacuum oven 70 C until fully molten and the bubbles have been removed. The syringe is inserted into a custom FDM printer. The syringe is heated to 80 C and can be mechanically or pneumatically driven. The computer aided design (CAD) files of the part to print is digitally sliced to create a STL file and transferred to the 3D printer. The polymer was printed using a straight steel nozzle with the diameter of 1.36 mm, at 30 mm/min, using 90 Psi air. The glass bed of the printer was cooled to ~0 C with no convection and was done using dry ice.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for manufacturing a three-dimensional object, the method comprising steps of:
   a) providing a digital description of the object as a set of voxels; and
   b) sequentially creating an actual set of voxels corresponding to the digital set of voxels; wherein at least one voxel comprises
      i) a polyurethane derived from: polyethylene glycol, polyethylene glycol-block-polypropylene glycol-block-polyethylene glycol polymer, polypropylene glycol-block-polyethylene glycol-block-polypropylene and mixtures thereof, 1,1'-Carbonyldiimidazole, polyamine of the structure:

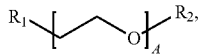

where $R_1$ is selected from the group consisting of: —OCH3, —OH, —NH2,

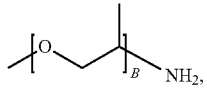

and mixtures thereof, $R_2$ is selected from the group consisting of: —(C2H4)-NH2, —CH3, —H,

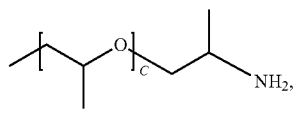

and mixtures thereof, A is between about 1 and about 300, (B+C)/A is between about 0 and about 0.6, and at least one $R_1$ or $R_2$ group contains nitrogen, and
      ii. a benefit agent;
   c) forming a three dimensional article wherein the three dimensional article dissolves in use.

2. The method according to claim 1 wherein the at least one voxel further comprises a filler.

3. The method according to claim 2 wherein the three-dimensional object comprises at least one void volume fully enclosed by voxels.

4. The method according to claim 3 wherein the void volume is at least partially filled with a solid, powder, liquid or mixtures thereof.

5. The method according to claim 2 wherein the three-dimensional object is a consumer product.

6. The method according to claim 1 wherein the benefit agent is an aversive agent.

* * * * *

SEQUENCE LISTING

```
<160> NUMBER OF SEQ ID NOS: 1

<210> SEQ ID NO 1
<211> LENGTH: 773
<212> TYPE: PRT
<213> ORGANISM: Bacillus sp.

<400> SEQUENCE: 1

Ala Glu Gly Asn Thr Arg Glu Asp Asn Phe Lys His Leu Leu Gly Asn
1               5                   10                  15

Asp Asn Val Lys Arg Pro Ser Glu Ala Gly Ala Leu Gln Leu Gln Glu
            20                  25                  30

Val Asp Gly Gln Met Thr Leu Val Asp Gln His Gly Glu Lys Ile Gln
        35                  40                  45

Leu Arg Gly Met Ser Thr His Gly Leu Gln Trp Phe Pro Glu Ile Leu
    50                  55                  60

Asn Asp Asn Ala Tyr Lys Ala Leu Ala Asn Asp Trp Glu Ser Asn Met
65                  70                  75                  80

Ile Arg Leu Ala Met Tyr Val Gly Glu Asn Gly Tyr Ala Ser Asn Pro
                85                  90                  95

Glu Leu Ile Lys Ser Arg Val Ile Lys Gly Ile Asp Leu Ala Ile Glu
            100                 105                 110

Asn Asp Met Tyr Val Ile Val Asp Trp His Val His Ala Pro Gly Asp
        115                 120                 125

Pro Arg Asp Pro Val Tyr Ala Gly Ala Glu Asp Phe Phe Arg Asp Ile
    130                 135                 140

Ala Ala Leu Tyr Pro Asn Asn Pro His Ile Ile Tyr Glu Leu Ala Asn
145                 150                 155                 160

Glu Pro Ser Ser Asn Asn Asn Gly Gly Ala Gly Ile Pro Asn Asn Glu
                165                 170                 175

Glu Gly Trp Asn Ala Val Lys Glu Tyr Ala Asp Pro Ile Val Glu Met
            180                 185                 190

Leu Arg Asp Ser Gly Asn Ala Asp Asp Asn Ile Ile Ile Val Gly Ser
        195                 200                 205

Pro Asn Trp Ser Gln Arg Pro Asp Leu Ala Ala Asp Asn Pro Ile Asn
    210                 215                 220

Asp His His Thr Met Tyr Thr Val His Phe Tyr Thr Gly Ser His Ala
225                 230                 235                 240

Ala Ser Thr Glu Ser Tyr Pro Pro Glu Thr Pro Asn Ser Glu Arg Gly
                245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Asn Gly Asp Gly Gly Pro
```

```
                275                 280                 285
Tyr Phe Asp Glu Ala Asp Val Trp Ile Glu Phe Leu Asn Glu Asn Asn
290                 295                 300
Ile Ser Trp Ala Asn Trp Ser Leu Thr Asn Lys Asn Glu Val Ser Gly
305                 310                 315                 320
Ala Phe Thr Pro Phe Glu Leu Gly Lys Ser Asn Ala Thr Asn Leu Asp
            325                 330                 335
Pro Gly Pro Asp His Val Trp Ala Pro Glu Glu Leu Ser Leu Ser Gly
            340                 345                 350
Glu Tyr Val Arg Ala Arg Ile Lys Gly Val Asn Tyr Glu Pro Ile Asp
            355                 360                 365
Arg Thr Lys Tyr Thr Lys Val Leu Trp Asp Phe Asn Asp Gly Thr Lys
370                 375                 380
Gln Gly Phe Gly Val Asn Ser Asp Ser Pro Asn Lys Glu Leu Ile Ala
385                 390                 395                 400
Val Asp Asn Glu Asn Asn Thr Leu Lys Val Ser Gly Leu Asp Val Ser
            405                 410                 415
Asn Asp Val Ser Asp Gly Asn Phe Trp Ala Asn Ala Arg Leu Ser Ala
            420                 425                 430
Asp Gly Trp Gly Lys Ser Val Asp Ile Leu Gly Ala Glu Lys Leu Thr
            435                 440                 445
Met Asp Val Ile Val Asp Glu Pro Thr Thr Val Ala Ile Ala Ala Ile
450                 455                 460
Pro Gln Ser Ser Lys Ser Gly Trp Ala Asn Pro Glu Arg Ala Val Arg
465                 470                 475                 480
Val Asn Ala Glu Asp Phe Val Gln Gln Thr Asp Gly Lys Tyr Lys Ala
            485                 490                 495
Gly Leu Thr Ile Thr Gly Glu Asp Ala Pro Asn Leu Lys Asn Ile Ala
            500                 505                 510
Phe His Glu Glu Asp Asn Asn Met Asn Asn Ile Ile Leu Phe Val Gly
            515                 520                 525
Thr Asp Ala Ala Asp Val Ile Tyr Leu Asp Asn Ile Lys Val Ile Gly
            530                 535                 540
Thr Glu Val Glu Ile Pro Val Val His Asp Pro Lys Gly Glu Ala Val
545                 550                 555                 560
Leu Pro Ser Val Phe Glu Asp Gly Thr Arg Gln Gly Trp Asp Trp Ala
            565                 570                 575
Gly Glu Ser Gly Val Lys Thr Ala Leu Thr Ile Glu Glu Ala Asn Gly
            580                 585                 590
Ser Asn Ala Leu Ser Trp Glu Phe Gly Tyr Pro Glu Val Lys Pro Ser
            595                 600                 605
Asp Asn Trp Ala Thr Ala Pro Arg Leu Asp Phe Trp Lys Ser Asp Leu
            610                 615                 620
Val Arg Gly Glu Asn Asp Tyr Val Ala Phe Asp Phe Tyr Leu Asp Pro
625                 630                 635                 640
Val Arg Ala Thr Glu Gly Ala Met Asn Ile Asn Leu Val Phe Gln Pro
            645                 650                 655
Pro Thr Asn Gly Tyr Trp Val Gln Ala Pro Lys Thr Thr Ile Asn
            660                 665                 670
Phe Asp Glu Leu Glu Glu Ala Asn Gln Val Asn Gly Leu Tyr His Tyr
            675                 680                 685
Glu Val Lys Ile Asn Val Arg Asp Ile Thr Asn Ile Gln Asp Asp Thr
            690                 695                 700
```

```
Leu Leu Arg Asn Met Met Ile Ile Phe Ala Asp Val Glu Ser Asp Phe
705                 710             715                 720

Ala Gly Arg Val Phe Val Asp Asn Val Arg Phe Glu Gly Ala Ala Thr
            725                 730                 735

Thr Glu Pro Val Glu Pro Glu Pro Val Asp Pro Gly Glu Glu Thr Pro
            740             745                 750

Pro Val Asp Glu Lys Glu Ala Lys Lys Glu Gln Lys Glu Ala Glu Lys
        755             760             765

Glu Glu Lys Glu Glu
    770
```